United States Patent [19]
Chaudhuri et al.

[11] Patent Number: 5,618,690
[45] Date of Patent: Apr. 8, 1997

[54] METHOD OF USING AN ER-LOCATED ENDOPROTEASE

[75] Inventors: Bhabatosh Chaudhuri, Münchenstein, Switzerland; Christine Stephan, Kingersheim, France; Peter Seeboth, Inzlingen, Germany; Howard Riezman, Biel-Benken, Switzerland

[73] Assignee: CIBA-Geigy Corporation, Tarrytown, N.Y.

[21] Appl. No.: 462,397

[22] Filed: Jun. 5, 1995

Related U.S. Application Data

[62] Division of Ser. No. 328,961, Oct. 24, 1994, Pat. No. 5,501,975, which is a continuation of Ser. No. 989,260, Dec. 11, 1992, abandoned.

[30] Foreign Application Priority Data

Dec. 16, 1991 [DE] Germany ............................... 91810984

[51] Int. Cl.$^6$ ............................... C12P 21/06; C12N 9/50
[52] U.S. Cl. ........................ 435/68.1; 435/69.1; 435/69.7; 435/219; 435/223
[58] Field of Search ................................. 435/68.1, 69.1, 435/69.7, 219, 223

[56] References Cited

FOREIGN PATENT DOCUMENTS

| | | |
|---|---|---|
| 0205404 | 12/1986 | European Pat. Off. . |
| 0212914 | 3/1987 | European Pat. Off. . |
| 0277313 | 8/1988 | European Pat. Off. . |
| 0327377 | 8/1989 | European Pat. Off. . |

OTHER PUBLICATIONS

Barr et al., "Expression and Processing of Biologically active Fibroblast Growth Factors in the Yeast *Saccharomyces cerevisiae*", *J. Biol. Chem.*, 263(31): 16471–16478, 1988.

Broach et al., "Transformation in Yeast: Development of a Hybrid Cloning Vector and Isolation of the CAN1 Gene", *Gene* 8: 121–133 (1979).

Chaudhuri et al., *FEBS LETTERS*, 304: 41–45 (1992).

Dean et al., *Biological Abstract* No. 91695, 90: 1006–1007 (1990).

Dean et al., *J. Cell. Biol.* 111: 369–377 (1990).

Felgner et al., "Lipofection: A highly efficient, lipid–mediated DNA–transfection procedure", *Proc. Natl. Acad. Sci.* 84: 7413–7417 (1987).

Fuller et al., "Yeast prohormone processing enzyme (KEX2 gene product) is a Ca$^{2+}$–dependent serine protease". *Proc. Natl. Acad. Sci.* 86: 1434–1438 (1989).

Fuller et al., *Science* 246:482–485 (1989).

Graham et al., *Virology*, 52:456–467 (1973).

Hinnen et al., "Heterologous Gene Expression in Yeast", *Yeast Genetic Engineering*, Butterworths Publishers, Stoneham, 193–213 (1989).

Klebe et al., "A general method for polyethylene–glycol–induced genetic transformation of bacteria and yeast", *Gene* 25:333–341 (1983).

Kurjan et al., "Structure of a Yeast Pheromone Gene (MFα): A Putative α–Factor Precursor Contains Four Tandem Copies of Mature α–Factor" *Cell*, 30:933–943 (1982).

Laemmli, U.K., "Cleavage of Structural Proteins during the Assembly of the Head of Bacteriophage T4", *Nature*, 227:680–685 (1970).

Mitani et al., *Yeast*, 6: 127–137 (1990).

Mizuno et al., "Yeast KEX2 Gene Encodes an Endopeptidase Homologous to Subtilisin–like Serine Proteases", *Biochem. Biophys. Res. Commun.*, 156:246–254 (1988).

Mullenbach et al., *Fed. Proc.* Abstract 42: 434 (1983).

Pelham, H.R.B., "Evidence that luminal ER proteins are sorted from secreted proteins in a post–ER compartment", *The EMBO Journal*, 7(4):913–918 (1988).

Pfeffer et al., "Biosynthetic Protein Transport and Sorting by the Endoplasmic Reticulum and Golgi", *Ann. Rev. Biochem.*, 56:829–852 (1987).

Rothstein, R., "Targeting, Disruption, Replacement, and Allele Rescue: Integrative DNA Transformation in Yeast", *Methods in Enzymology*, 194: 281–302 (1991).

Sanger et al., "DNA sequencing with chain–terminating inhibitors", *Proc. Natl. Acad. Sci.*, 74:5463–5467 (1977).

Steube et al., "α–Factor–leader–directed secretion of recombinant human–insulin–like growth factor I from *Saccharomyces cerevisiae*", *Eur. J. Biochem.*, 198: 651–657 (1991).

von Heijne, "A new method for predicting signal sequence cleavage sites", *Nucleic Acids Research*, 14(11):4683–4690 (1986).

Zoller et al., "Oligonucleotide–Directed Mutagenesis: A Simple Method using Two Oligonucleotide Primers and a Single–Stranded DNA Template", *Methods in Enzymology*, 154: 329–350 (1987).

*Primary Examiner*—Keith D. Hendricks
*Attorney, Agent, or Firm*—James Scott Elmer; Henry P. Nowak

[57] ABSTRACT

The invention concerns novel DNA molecules encoding a modified, endoplasmic reticulum-located "dibasic processing endoprotease" and the use of said endoplasmic reticulum-located "dibasic processing endoprotease" for the correct processing of heterologous polypeptides in transformed hosts.

5 Claims, No Drawings

METHOD OF USING AN ER-LOCATED ENDOPROTEASE

This is a divisional application of Ser. No. 08/328,961, filed Oct. 24, 1994, now U.S. Pat. No. 5,501,975, which is a continuation of Ser. No. 07/989,260, filed Dec. 11, 1992, now abandoned.

The invention concerns novel DNA molecules encoding a modified, endoplasmic reticulum-located "dibasic processing endoprotease" and the use of said endoplasmic reticulum-located "dibasic processing endoprotease" for the correct processing of heterologous polypeptides in transformed hosts.

BACKGROUND OF THE INVENTION

The production of pharmaceutically applicable or enzymatically active proteins is a key area in the rapidly developing biotechnology industry. Since the beginning of the era of recombinant DNA technology a great number of valuable heterologous proteins have been produced in and secreted from eukaryotic host cells which had been transformed with suitable expression vectors containing DNA sequences coding for said proteins. One of the major problems with the production of secreted proteins in eukaryotic expression systems is to avoid malfolded biologically inactive product.

It is now generally accepted that proteins destined for secretion from eukaryotic cells are translocated to the endoplasmic reticulum (ER) due to the presence of a signal sequence which is cleaved off by the enzyme signal peptidase located in the rough ER membrane. The protein is then transported from the ER to the Golgi and via Golgi derived secretory vesicles to the cell surface (S. Pfeffer and J. Rothman, Ann. Rev. Biochem. 56:829–52, 1987). Another major step in the production of correctly processed and correctly folded proteins is the conversion of proproteins to the mature forms in the Golgi apparatus and secretory vesicles. The cleavage of the proprotein occurs at a so-called dibasic site, i.e. a motif consisting of at least two basic amino acids. The processing is catalysed by enzymes located in the Golgi-apparatus, the so-called "dibasic processing endoproteases".

There are different "dibasic processing endoproteases" known which are involved in the processing of protein precursors, for example the mammalian proteases furin, PC2, PC1 and PC3, and the product of the yeast YAP3 gene and yeast yscF (also named KEX2 gene product; herein referred to as KEX2p).

KEX2p is involved in the maturation of the yeast mating pheromone α-factor (J. Kurjan and I. Hershkowitz, Cell 30:933–943, 1982). The α-factor is produced as a 165 amino acid precursor which is processed during the transport to the cell surface. In the first step, the 19-amino acid signal sequence (pre-sequence) is cleaved off by the signal peptidase. Then the precursor is glycosylated and moves to the Golgi where a 66-amino acid pro-sequence is cut off by KEX2p. The α-factor pre-pro-sequence is also known as α-factor "leader" sequence. A second protease in the Golgi apparatus, i.e. the KEX1 gene product, is responsible for the final maturation of the protein.

KEX2p is encoded by the KEX2 gene and consists of a N-terminal catalytic domain, a Ser/Thr rich domain, a membrane-spanning domain and a C-terminal tail responsible for Golgi localization. Mutant KEX2p enzyme lacking 200 C-terminal amino acids, including the Ser/Thr rich domain, the membrane spanning domain and the C-terminal tail, still retains KEX2p protease function, viz. cleavage at the C-terminal side of a pair of basic amino adds, such as Lys-Arg or Arg-Arg [Fuller et al., 1989, Proc. Natl. Acad. Sci. 86, 1434–1438; Fuller et al., 1989, Science 246, 482–485].

Leader sequences such as the yeast a-factor leader sequence are widely used for the production of secreted heterologous proteins in eukaryotic cells. In many cases, however, great difficulties are encountered because considerable amounts of biologically inactive proteins are produced due to malfolding and aggregation of the proteins, especially in the case of low molecular weight proteins.

OBJECT OF THE INVENTION

Surprisingly, it has been found that a higher ratio of biologically active correctly folded heterologous protein to inactive malfolded protein is produced in the host cell if the host cell has a "dibasic processing endoprotease" activity in the endoplasmic reticulum (ER).

Thus, it is an object of the invention to provide a method for the preparation of heterologous biologically active protein comprising the use of a host cell having a "dibasic processing endoprotease" in the ER. Other objects are the provision of a host cell having a "dibasic processing endoprotease" variant which is located in the ER due to the transformation with a gene encoding the "dibasic processing endoprotease" variant, further the provision of a DNA molecule comprising such a gene, and the provision of methods for the preparation of such a DNA molecule and of such a host cell.

DETAILED DESCRIPTION OF THE INVENTION

Process for the Preparation of Heterologous Protein

The invention concerns a process for the preparation of heterologous biologically active protein liberated in the host cell from a proprotein, said process comprising the use of a host cell having a "dibasic processing endoprotease" activity in the ER.

A "dibasic processing endoprotease" activity within the meaning of the present invention is the activity of an endoprotease specific for a motif of two basic amino acids, e.g. Arg-Arg, Arg-Lys, Lys-Arg or Lys-Lys, which endoprotease is naturally located in the Golgi apparatus and is naturally involved in the processing of proproteins or polyproteins.

The term "dibasic processing endoprotease" includes eukaryotic enzymes such as of mammalian origin, e.g. furin, PC2, PC1, PC3 (Barr, Cell 66:1–3, 1991), and preferentially enzymes derived from yeast, such as the YAP3 endoprotease [Egel-Mitani et al., Yeast 6: 127–137(1990)] and, most preferentially the *S. cerevisiae* endoprotease KEX2p.

The biologically active variants of the "dibasic processing endoprotease" of the invention are not restricted to the Golgi apparatus but are located in the ER due to the presence of an ER retention signal, i.e. a structure which is suitable for the retention of a "dibasic processing endoprotease" in the ER. The naturally occurring "dibasic processing endoproteases" are attached to the membrane of the Golgi apparatus or secretory vesicles due to a membrane anchor, i.e. a hydrophobic membrane-spanning sequence. The ER retention signals are to be linked to the C-terminus of the protein, i.e. the "dibasic processing endoprotease" in order to locate the protease in the ER. Such a fusion protein consists of a protease and an ER retention signal is hereinafter called "ER-located dibasic processing endoprotease".

In a preferred embodiment of the invention the ER retention signal is attached to the C-terminus of a soluble form of a "dibasic processing endoprotease", i.e. a variant of a "dibasic processing endoprotease" which is not attached to a cell membrane. Such a soluble form lacks the hydrophobic membrane spanning sequence but still retains the typical enzymatic "dibasic processing" function.

A preferred example of a soluble "dibasic processing endoprotease" useful in the present invention is a soluble *S. cerevisiae* KEX2p, i.e. a KEX2p variant lacking the hyrophobic membrane-spanning sequence located in the region $Tyr^{679}$ to $Met^{699}$ [the amino acid sequence of the 814-residue *S. cerevisiae* KEX2p is known from K. Mizuno et al., Biochem. Biophys. Res. Commun. 156, 246–254 (1988)]. In particular, in a soluble KEX2p endoprotease according to the invention, the membrane binding site has selectively been removed. Hence the C-terminus starting with, for example, amino acid 700 (Lys) is still present, or the whole C-terminus including the membrane binding site, i.e. 136 to approximately 200 amino acids from the C-terminus, has been removed. Such soluble X2p proteins are described, for example, in EP 327,377 or in R. S. Fuller et at., Proc. Natl. Acad. Sci. USA 86, 1434–1438 (1989). The most preferred soluble "dibasic processing endoprotease" of the invention is the soluble KEX2p having the sequence depicted in the sequence listing under SEQ ID No. 1 and is hereinafter referred to as $KEX2p_s$.

An ER-retention signal is a structure determining the location of a polypeptide in the ER. The location in the ER may be based on a specific attachment to the ER membrane or preferentially on the prevention of the transport of a soluble protein into the Golgi apparatus by retransportation of the polypeptide from a compartment between the Golgi apparatus and the ER into the ER lumen. ER retention signals used preferentially in the present invention are of the latter type, i.e. such preventing the transport of soluble protein to the Golgi apparatus.

A preferred example of such an ER retention signal is the so-called KDEL sequence (SEQ ID No. 3) functional in mammalian cells. More preferred is the DDEL sequence (SEQ ID No. 4) functional in the yeast *Kluyveromyces lactis* and most preferred is the HDEL sequence (SEQ ID No. 2) functional in *S. cerevisiae* and in *K. lactis*.

Preferred forms of the "ER-located dibasic processing endoprotease" comprise the ER-retention signal KDEL sequence attached to a "dibasic processing endoprotease" of a mammalian cell such as, for example, furin, PC1, PC2 or PC3 (P. J. Bart, supra), or preferably to a soluble variant thereof, or also to a *S. cerevisiae* KEX2p, which latter is known to be functional in mammalian cells, or preferably to a soluble variant thereof. If such an "ER-located dibasic processing endoprotease", e.g. furinKDEL, PC1KDEL PC2KDEL, PC3KDEL or KEX2pKDEL enzymes, are produced in a mammalian host cell transformed with a gene for the expression of a heterologous protein, a higher proportion of correctly folded, secreted heterologous protein is produced.

More preferably, the DDEL retention signal is fused to a *K. lactis* KEX2p analog or preferably to a soluble variant thereof, or to a *S. cerevisiae* KEX2p or preferably to a soluble variant thereof, in particular to $KEX2p_s$. *S. cerevisiae* KEX2p is functional also in *K. lactis*. Such a KEX2pDDEL produced in a *K. lactis* host cell allows the expression of a higher proportion of correctly folded, secreted heterologous protein.

Most preferably, the HDEL retention signal is fused to a *S. cerevisiae* KEX2p, or preferably to a soluble variant thereof, in particular to $KEX2p_s$. Such a KEX2pHDEL protein produced in a *K. lactis* or, more preferably, in a *S. cerevisiae* host cell allows the expression of a higher proportion of correctly folded, secreted heterologous protein.

In order to produce a host cell in which an "ER-located dibasic processing endoprotease" is produced, the host cell must be transformed with an expression cassette encoding an "ER-located dibasic processing endoprotease". The host cell which is transformed may still contain an intact endogeneous gene for the endogeneous dibasic processing endoprotease on the chromosome, i.e. in the case of the *S. cerevisiae* system the host cell which is to be transformed with KEX2pHDEL may be a $\underline{KEX2^+}$ cell, e.g. strain AB110. However, gene coding for the corresponding endogeneous dibasic processing endoprotease may also be destroyed, i.e. in the case of the *S. cerevisiae* system the host cell may be a $\underline{kex2^-}$ cell, e.g. strain AB110 $\underline{kex2^-}$.

For the transformation of a host cell hybrid vectors are used which provide for replication and expression of an expression cassette encoding the "ER-located dibasic processing endoprotease". These hybrid vectors may be extrachromosomally maintained vectors or also vectors which are integrated into the host genome so that a cell is produced which is stably transformed with a said expression cassette. Suitable extrachromosomally maintained vectors and also vectors integrating in to the host genome the transformation of mammalian cells or of yeast cells are well known in the art.

The hybrid vectors may be derived from any vector useful in the art of genetic engineering, such as from viruses, plasmids or chromosomal DNA, such as derivatives of SV40, Herpes-viruses, Papilloma viruses, Retroviruses, Baculovirus, or derivatives of yeast plasmids, e.g. yeast 2 μ plasmid.

Several possible vector systems are available for integration and expression of the cloned DNA of the invention. In principle, all vectors which replicate and/or express a desired polypeptide gene comprised in an expression cassette of the invention in the chosen host are suitable. The vector is selected depending on the host cells envisaged for transformation. Such host cells are preferably mammalian cells (if a "dibasic processing endoprotease" functional in mammalian cells is used) or, more preferably, yeast cells (if a "dibasic processing endoprotease" functional in yeast cells is used). In principle, the extrachromosomally maintained hybrid vectors of the invention comprise the expression cassette for the expression of an ER-located "dibasic processing endoprotease", and an origin of replication or an autonomously replicating sequence.

An origin of replication or an autonomously replicating sequence (a DNA element which confers autonomously replicating capabilities to extrachromosomal elements) is provided either by construction of the vector to include an exogeneous origin such as, in the case of the mammalian vector, derived from Simian virus (SV 40) or another viral source, or by the host cell chromosomal mechanisms.

A hybrid vector of the invention may contain selective markers depending on the host which is to be transformed, selected and cloned. Any marker gene can be used which facilitates the selection of transformants due to the phenotypic expression of the marker. Suitable markers am particularly those expressing antibiotic resistance, e.g. against tetracycline or ampicillin, or genes which complement host lesions. It is also possible to employ as markers structural genes which are associated with an autonomously replicating segment providing that the host to be transformed is auxotrophic for the product expressed by the marker.

Preferred vectors suitable for the preparation of hybrid vectors of the invention, i.e. comprising an expression cassette for the preparation of an ER-located "dibasic processing endoprotease" are those which are suitable for replication and expression in *S. cerevisiae* and contain a yeast-replication origin and a selective genetic marker for yeast. Hybrid vectors that contain a yeast replication origin, for example the chromosomal autonomously replicating segment (ARS), are retained extrachromosomally within the yeast cell after transformation and are replicated autonomously during mitosis. Also, hybrid vectors that contain sequences homologous to the yeast 2 μ plasmid DNA or that contain ARS and a sequence of a chromosomal centromere, for example CEN4, can be used. Preferred are the 2 μ based plasmids containing the complete or partial *S. cerevisiae* 2 μ plasmid sequence. Suitable marker genes for yeast are especially those that impart antibiotic resistance to the host or, in the case of auxotrophic yeast mutants, genes that complement the host lesions. Corresponding genes impart, for example, resistance to the antibiotic cycloheximide or provide for prototrophy in an auxotrophic yeast mutant, for example the URA3, LEU2, HIS3 or the TRP1 gene.

Preferably, hybrid vectors furthermore contain a replication origin and a marker gene for a bacterial host, especially *E. coli*, so that the construction and the cloning of the hybrid vectors and their precursors can be carried out in *E. coli*.

In a most preferred embodiment of the invention a kex2⁻ strain of *S. cerevisiae* is transformed either with an extrachromosomally maintained plasmid or with integration plasmid comprising an expression cassette for the expression of a soluble KEX2pHDEL.

An "expression cassette" for the expression of an ER-located "dibasic processing endoprotease" means a DNA sequence capable of expressing such a polypeptide and comprises a promoter and a structural gene and, if desired, a transcriptional terminator and optionally a transcriptional enhancer, ribosomal binding site and/or further regulatory sequences.

Such an expression cassette may contain either the regulatory elements naturally linked with the corresponding "dibasic processing endoprotease" gene, heterologous regulatory elements or a mixture of both, i.e., for example, a homologous promoter and a heterologous terminator region.

A wide variety of promoter sequences may be employed, depending on the nature of the host cell. Sequences for the initiation of translation are for example Shine-Dalgarno sequences. Sequences necessary for the initiation and termination of transcription and for stabilizing the mRNA are commonly available from the noncoding 5'-regions and 3'-regions, respectively, of vital or eukaryotic cDNAs, e.g. from the expression host.

Examples for promoters are as above, i.e. yeast TRPI-, ADHI-, ADHII-, CYC1, GAL1/10, CUP1, PHO3-, or PHO5-promoter, or promoters from heat shock proteins, or glycolytic promoters such as glyceraldehyde-3-phosphate dehydrogenase (GAP) promoter (including 5' truncated GAP) or a promoter of the enolase, 3-phosphoglycerate kinase (PGK), hexokinase, pyruvate decarboxylase, phosphofructokinase, glucose-6-phosphate isomerase, 3-phosphoglycerate mutase, pyruvate kinase, triosephosphate isomerase, phosphoglucose isomerase and glucokinase genes, furthermore α-factor promoter and hybrid promoters, such as hybrid PH05-GAP or ADH2-GAP promoters or hybrid promoters using heat shock elements.

Promoters suitable for the expression in mammalian cells are, for example, derived from viruses, e.g. SV40, Rous sarcoma virus, adenovirus 2, bovine papilloma virus, papovavirus, cytomegalovirus derived promoters, or are mammalian cell derived promoters, e.g. of the actin, collagen, myosin, or β-globin gent. The yeast promoters may be combined with enhancing sequences such as the yeast upstream activating sequences (UAS) and the promoters active in mammalian cells may be combined with viral or cellular enhancers such as the cytomegalovirus IE enhancers, SV40 enhancer, immunoglobulin gene enhancer or others.

Enhancers are transcription-stimulating DNA sequences, e.g. derived from viruses such as Simian virus, polyoma virus, bovine papilloma virus or Moloney sarcoma virus, or of genomic origin. An enhancer sequence may also be derived from the extrachromosomal ribosomal DNA of *Physarum polycephalum*, or it may be the upstream activation site from the yeast acid phosphatase PH05 gene, or the yeast PH05, TRP, PH05-GAPDH hybrid, or the like promoter.

A host cell of the invention having a "dibasic processing endoprotease" activity in the ER is useful for the preparation of correctly processed heterologous proteins. For this purpose an expression cassette for the expression of a gene encoding the desired heterologous protein is of course also to be introduced into the host cell. Such an expression cassette is herein named "production gene".

Such a production gene comprises a promoter region, a DNA sequence encoding signal peptide which can be cleaved off by a signal peptidase, a DNA sequence encoding a pro-sequence which can be cleaved off from the desired heterologous gene product by a "dibasic processing endoprotease", a DNA sequence encoding a desired heterologous gene product and/or a transcriptional terminator region and optionally a transcriptional enhancer, ribosomal binding site and/or further regulatory sequences. The coding regions for signal peptide, the pro-sequence and the heterologous protein are attached "in frame", i.e. the signal peptide is after the translation of the structural gene covalently linked to the N-terminus of the pro-sequence and the latter is after the translation of the gene covalently linked to the N-terminus of the heterologous protein.

The pro-sequence can be any sequence from a random genomic library of fragments which can act as a molecular chaperone, i.e. a polypeptide which in cis or in trans can influence the formation of an appropriate conformation. Preferably, it is a random sequence which allows membrane translocation. In particular preferred is the α-factor prosequence.

As in the expression cassette described above for the expression of a "dibasic processing endoprotease", a wide variety of regulator sequences may be employed, depending on the nature of the host cell For example, promoters that are strong and at the same time well regulated are the most useful. Sequences for the initiation of translation are for example Shine-Dalgarno sequences. Sequences necessary for the initiation and termination of transcription and for stabilizing the mRNA are commonly available from the noncoding 5'-regions and 3'-regions, respectively, of viral or eukaryotic cDNAs, e.g. from the expression host.

Signal peptides within the meaning of the present invention are presequences directing the translocation of the desired polypeptide to the ER, for example the α-factor signal sequence. Further signal sequences are known from literature, e.g. those compiled in von Heijne, G., Nucleic Acids Res. 14, 4683 (1986).

Examples for suitable promoters are as above, i.e. yeast TRPI-, ADHI-, ADHII-, CYC1, GAL1/10, CUP1, PHO3-, or PHO5-promoter, or promoters from heat shock proteins, or glycolytic promoters such as glyceraldehyde-3-phosphate dehydrogenase (GAP) promoter (including 5' truncated GAP) or a promoter of the enolase, 3-phosphoglycerate kinase (PGK), hexokinase, pyruvate decarboxylase, phosphofructokinase, glucose-6-phosphate isomerase, 3-phosphoglycerate mutase, pyruvate kinase, triosephosphate isomerase, phosphoglucose isomerase and glucokinase genes, furthermore α-factor promoter and hybrid promoters, such as hybrid PH05-GAP or ADH2-GAP promoters or hybrid promoters using heat shock elements, or promoters derived from eukaryotic viruses, e.g. SV40, Rous sarcoma virus, adenovirus 2, bovine papilloma virus, papovavirus, cytomegalovirus derived promoters or mammalian cell derived promoters, e.g. of the actin, collagen, myosin, or β-globin gene. The eukaryotic promoters may be combined with enhancing sequences such as the yeast upstream activating sequences (UAS) or vital or cellular enhancers such as the cytomegalovirus IE enhancers, SV40 enhancer, immunoglobulin gene enhancer or others.

The expression cassette encoding the ER-located "dibasic processing endoprotease" and the production gene may comprise promoters of the same or of different types. For example, they may both be regulated by an inducible promoter which allows the concerted expression of the precursor of the heterologous protein and of the ER-located "dibasic processing endoprotease" processing it.

In a preferred embodiment of the invention a production gene suitable for the expression in a *S. cerevisiae* cell which cell contains an ER-located "dibasic processing endoprotease", preferably YAP3pHDEL, more preferably KEX2pHDEL or, most preferably, KEX2p₃HDEL comprises a structural fusion gene composed of a DNA sequence encoding a yeast pro-sequence which can be cleaved off from the precursor by a yeast "dibasic processing endoprotease", preferably the *S. cerevisiae* α-factor leader sequence and downstream a DNA sequence coding for a desired heterologous protein, said fusion gene being under the control of expression control sequences regulating transcription and translation in yeast.

The heterologous protein may be any protein of biological interest and of prokaryotic or especially eukaryotic, in particular higher eukaryotic such as mammalian (including animal and human), origin and is, for example, an enzyme which can be used, for example, for the production of nutrients and for performing enzymatic reactions in chemistry or molecular biology, or a protein which is useful and valuable for the treatment of human and animal dims or for the prevention thereof, for example a hormone, polypeptide with immunomodulatory, anti-vital and anti-tumor properties, an antibody, viral antigen, blood clotting factor, a fibrinolytic agent, a growth regulation factor, furthermore a foodstuff and the like.

Example of such proteins am e.g. hormones such as secret, thymosin, relaxin, calcitonin, luteinizing hormone, parathyroid hormone, adrenocorticotropin, melanocyte-stimulating hormone, β-lipotropin, urogastrone, insulin, growth factors, such as epidermal growth factor (EGF), insulin-like growth factor (IGF), e.g. IGF-1 and IGF-2, mast cell growth factor, nerve growth factor, glia derived nerve cell growth factor, platelet derived growth factor (PDGF), or transforming growth factor (TGF), such as TGFβ, growth hormones, such as human or bovine growth hormones, interleukin, such as interleukin-1 or -2, human macrophage migration inhibitory factor (MIF), interferons, such as human α-interferon, for example interferon-αA, αB, αD or αF, β-interferon, γ-interferon or a hybrid interferon, for example an αA-αD- or an αB-αD-hybrid interferon, especially the hybrid interferon BDBB, proteinase inhibitors such as α₁-antitrypsin, SLPI and the like, hepatitis virus antigens, such as hepatitis B virus surface or core antigen or hepatitis A virus antigen, or hepatitis nonA-nonB antigen, plasminogen activators, such as tissue plasminogen activator or urokinase, hybrid plasminogen activators, such as K₂tuPA, tick anticoagulant peptide (TAP), tumour necrosis factor, somatostatin, renin, immunoglobulins, such as the light and/or heavy chains of immunoglobulin D, E or G, or human-mouse hybrid immunoglobulins, immunoglobulin binding factors, such as immunoglobulin E binding factor, human calcitonin-related peptide, blood clotting factors, such as factor IX or VIIIc, platelet factor 4, crythropoietin, eglin, such as eglin C, desulfatohirudin, such as desulfatohirudin variant HV1, HV2 or PA, corticostatin, echistatin, cystatins, human superoxide dismutase, viral thymidin kinase, β-lactamase or glucose isomerase. Preferred are human α-interferon e.g. interferon αB, or hybrid interferon, particularly hybrid interferon BDBB (see EP 205,404), human tissue plasminogen activator (t-PA), human single chain urokinase-type plasminogen activator (scu-PA), hybrid plasminogen activator K₂tuPA (see EP 277,313), human calcitonin, desulfatohirudin, e.g. variant HV1, even more preferred insulin-related proteins such as insulin, relaxin, the even more preferred insulin-like growth factor H and, in particular, insulin-like growth factor I. Proteins containing a pair of basic amino acids, such as Arg-Arg, Lys-Arg, Lys-Lys and Arg-Lys, exposed on the protein surface and therefore amenable to proteolytic cleavage, are not suited for the process according to the invention and will have to be mutated such that one of the consecutive basic amino acids is replaced by another non-basic amino acid without affecting the biological activity.

A production gene needs not necessarily be located on the same vector molecule as the gene encoding the ER-located "dibasic processing endoprotease". In the case the latter is located on a vector which is extrachromosomally maintained, it may, be advantageous if the production gene is located on the same vector molecule.

Expression vectors suitable for the expression of a production gene are, for example, also those which are described above as being suitable for the expression of an ER-located "dibasic processing endoprotease", i.e. vectors derived from any vector useful in the art of genetic engineering, such as from viruses, plasmids or chromosomal DNA, such as derivatives of SV40, Herpes-viruses, Papilloma viruses, Retroviruses, Baculovirus, or derivatives of yeast plasmids, e.g. yeast 2 µ plasmid. Preferred are vectors for replication and expression in *S. cerevisiae*.

Preferably, the hybrid vectors of the present invention also contain a replication origin and a marker gene for a bacterial host, especially *E. coli*, so that the construction and the cloning of the hybrid vectors and their precursors can be carried out in *E. coli*.

A process for the preparation of heterologous biologically active protein comprising the use of a host cell having a "dibasic processing endoprotease" activity in the ER according to the invention comprises (a) transforming a suitable host cell with a hybrid vector comprising an expression cassette encoding an ER-located "dibasic processing endoprotease" and with a hybrid vector encoding a production gene, or (b) transforming a suitable host cell with a hybrid vector comprising both an expression cassette encoding an ER-located "dibasic processing endoprotease" and a production gene, or (c) transforming a suitable host cell which is stably transformed with a gene encoding an ER-located "dibasic processing endoprotease" with a hybrid vector encoding a production gene, culturing the transformed host cells under conditions in which the gene encoding the ER-located "dibasic processing endoprotease" and the production gene are expressed, and isolating the desired heterologous polypeptide from the culture medium according to conventional methods.

The invention preferentially concerns a process wherein a yeast strain, more preferably a *Saccharomyces cerevisiae* strain, e.g. AB110 or AB110 kex2⁻, an ER-located yeast "dibasic processing endoprotease", e.g. YAP3DDEL or, preferably, YAP3HDEL or, more preferably, KEX2pHDEL, most preferably KEX2p$_s$HDEL, is used for the preparation of an insulin-like protein, preferably IGF-2 and, more preferably, IGF-1, which is produced as a precursor containing the α-factor leader sequence.

The transformation is accomplished by methods known in the art, for example, according to the method described by Hinnen et al [Proc. Natl. Acad. Sci. USA 75, 1919(1978)]. This method can be divided into three steps:

(1) Removal of the yeast cell wall or parts thereof.

(2) Treatment of the "naked" yeast cells (spheroplasts) with the expression vector in the presence of PEG (polyethyleneglycol) and $Ca^{2+}$ ions.

(3) Regeneration of the cell wall and selection of the transformed cells in a solid layer of agar.

The transformed host cells are cultured by methods known in the art in a liquid medium containing assimilable sources of carbon, nitrogen and inorganic salts. Various sources of carbon can be used for culture of the transformed yeast cells according to the invention. Examples of preferred sources of carbon are assimilable carbohydrates, such as glucose, maltose, mannitol or lactose, or an acetate, which can be used either by itself or in suitable mixtures. Examples of suitable sources of nitrogen are amino acids, such as casaminoacids, peptides and proteins and their degradation products, such as tryptone, peptone or meat extracts, yeast extracts, malt extract and also ammonium salts, for example ammonium chloride, sulfate or nitrate, which can be used either by themselves or in suitable mixes. Inorganic salts which can also be used are, for example, sulfates, chlorides, phosphates and carbonates of sodium, potassium, magnesium and calcium. The medium furthermore contains, for example, growth-promoting substances, such as trace elements, for example iron, zinc, manganese and the like, and preferably substances which exert a selection pressure and prevent the growth of cells which have lost the expression plasmid. Thus, for example, if a yeast strain which is auxotrophic in, for example, an essential amino acid, is used as the host microorganism, the plasmid preferably contains a gene coding for an enzyme which complements the host defect. Cultivation of the yeast strain is performed in a minimal medium deficient in said amino acid.

Culturing is effected by processes which are known in the art. The culture conditions, such as temperature, pH value of the medium and fermentation time, are chosen such that a maximum titre of the heterologous proteins prepared according to the invention is obtained. Thus, the yeast strain is preferably cultured under aerobic conditions by submerged culture with shaking or stirring at a temperature of about 20° to 40° C., preferably about 30° C., and a pH value of 5 to 8, preferably at about pH 7, for about 4 to about 96 hours, preferably until maximum yields of the proteins of the invention are reached. The culture medium is selected in such a way that selection pressure is exerted and only those cells survive which still contain the hybrid vector DNA including the genetic marker. Thus, for example, an antibiotic is added to the medium when the hybrid vector includes the corresponding antibiotic resistance gene.

When the cell density has reached a sufficient value culturing is interrupted and the medium containing the product is separated from the cells which can be provided with fresh medium and used for continuous production. The protein can also accumulate within the cells, especially in the periplasmic space. In the latter case the first step for the recovery of the desired protein consists in liberating the protein from the cell interior. The cell wall is first removed by enzymatic digestion with glucosidases or, alternatively, the cell wall is removed by treatment with chemical agents, i.e. thiol reagents or EDTA, which give rise to cell wall damages permitting the produced protein to be released. The resulting mixture is enriched for heterologous protein by conventional means, such as removal of most of the non-proteinaceous material by treatment with polyethyleneimine, precipitation of the proteins using ammonium sulphate, gel electrophoresis, dialysis, chromatography, for example, ion exchange chromatography (especially preferred when the heterologous protein includes a large number of acidic or basic amino acids), size-exclusion chromatography, HPLC or reverse phase HPLC, molecular sizing on a suitable Sephadex® column, or the like. The final purification of the pre-purified product is achieved, for example, by means of affinity chromatography, for example antibody affinity chromatography, especially monoclonal antibody affinity chromatography using antibodies fixed on an insoluble matrix by methods known in the art.

Recombinant DNA Molecules

The invention also concerns a recombinant DNA molecule encoding an expression cassette for an ER-located "dibasic processing endoprotease" as defined above. The invention timber concerns hybrid vectors comprising such a recombinant DNA molecule.

The present invention preferably concerns a recombinant DNA molecule or hybrid vector comprising the coding region for KEX2p, preferentially for a soluble KEX2p variant, most preferably for KEX2p$_s$ shown in the sequence listing under SEQ ID No. 1, and for an ER retention signal, preferentially for the HDEL sequence shown in the sequence listing under SEQ ID No. 2. The coding sequence for the ER retention signal is preferentially located in downstream direction of the KEX2p coding region. A KEX2p with HDEL attached at the C-terminus is herein named KEX2pHDEL, the corresponding structural gene is KEX$_2$HDEL.

As mentioned above some soluble KEX2p variants are known from the literature. Further deletion mutants according to the invention can be prepared using methods known in the art, for example by preparing a corresponding DNA coding for said mutant, inserting it in a suitable vector DNA under the control of an expression control sequence, transforming suitable host microorganisms with the expression vector formed, culturing the transformed host microorganism in a suitable culture medium and isolating the produced mutant. The DNA coding for any of said mutants can be produced for example, by taking a plasmid containing the DNA coding for KEX2p and (1) digesting it with a restriction enzyme which cleaves within or 3' of the DNA region coding for the membrane binding site (for example, EcoRI, BstXI or NarI), digesting the cleaved DNA with a suitable endonuclease, for example Bal31, such that said DNA region is removed and recircularizing the linearized plasmid by blunt end ligation or the like, or (2) choosing or creating (for example by site-directed mutagenesis) one restriction site 5' to and one restriction site 3' to the DNA region coding for the membrane binding site (for example PvuII and NarI or EcoRI; the 3' restriction site may also be located within the plasmid DNA adjacent to the translation stop signal of the KEX2 gene), digesting the plasmid with two restriction enzymes recognizing said restricting sites and recirculating the linearized plasmid by blunt end ligation or the like, or (3) deleting the DNA region coding for the membrane binding site by using loop-out mutagenesis, or (4) totally deleting the C-terminus by digesting with PvuII in the case of KEX2 and recirculating the linearized plasmid by blunt end ligation or the like. As the DNA sequences of KEX2 are known (K. Mizumo et al. supra) a suitable mutagenic oligonucleotide can easily be devised and used to delete said DNA region applying the M13 cloning system. Care must be taken that the mutated KEX2 genes are linked with a DNA sequence encoding a yeast ER retention signal. Such a DNA sequence can be introduced at the desired place via a synthetic linker DNA or it may be provided by the adjacent vector DNA. Preferentially, the mutated KEX2 genes include at their 3' ends codons which code for the HDEL sequence defined above. All of these methods make use of conventional techniques.

Within the scope of the present invention are also recombinant DNA molecules comprising DNA sequences which are degenerate within the meaning of the genetic code to the DNA sequences with SEQ ID No. 1 and 2, i.e. DNA sequences encoding the same amino acid sequences although nucleotides are exchanged. Such degenerate DNA sequences may, for example, contain new restriction enzyme cleavage sites.

Host Strains

Another aspect of the present invention involves host cells, preferably mammalian, more preferably yeast, even more preferably *K. lactis* and most preferably *S. cerevisiae* cells transformed with a hybrid vector of the invention comprising an expression cassette encoding an ER-located "dibasic processing endoprotease". The invention also concerns host cells which are stably transformed with an expression cassette encoding an ER-located "dibasic processing endoprotease", i.e. which comprise such a recombinant expression cassette integrated into a chromosome.

Suitable hosts for the integration of an expression cassette encoding KEX2HDEL are e.g. kex2⁻ mutants of yeast, preferentially of *S. cerevisiae*. The method for the preparation of transformed host cells comprises transforming host cells with an integration vector consisting of a KEX2pHDEL expression cassette which is under the control of any constitutive or inducible promoter, preferably of the promoters defined above or of the promoter of the KEX2 gene, and selecting stably transformed cells. Stable integrative transformation is state of the art and can be performed, for example, according to the procedured reported for mammalian cells in P. L. Felgner et al., Proc. Natl. Acad. Sci USA 84:7413–7417(1987) or in F. L. Graham et al., Virology 52:456–467(1973) and for *S. cerevisiae* cells in R. Rothstein, Methods Enzymol. 194:281–302(1991).

The invention concerns especially the recombinant DNA molecules, the hybrid vectors, the transformed hosts, the proteins and the methods for the preparation thereof and the method for the preparation of a biologically active protein as described in the examples.

The following examples serve to illustrate the invention but should not be construed as a limitation thereof.

EXAMPLE 1

Construction of a shortened KEX2 gene encoding soluble KEX2p variant

In order to get a soluble KEX2p protease activity, a mutant KEX2 gene lacking 600 bp, coding for the C terminal 200 amino acids, is constructed. The truncated gene is under the control of the KEX2 promoter reaching from −1 to −502. Translation is terminated at a stop codon (TAA) originating from the polylinker of pUC18.

In detail, plasmid pUC19 [Boehringer Mannheim GmbH, FRG] is digested to completion with HindIII and the 2686 bp fragment is isolated. The ends are filled in and the fragment is religated. An aliquot of the ligation mixture is added to calcium-treated, transformation competent *E. coli* JM101 [Invitrogen, San Diego, USA] cells. 12 transformed ampicillin resistant *E. coli* transformants are grown in the presence of 100 µg/ml ampicillin. Plasmid DNA is prepared and analysed by digestion with HindIII as well as with BamHI. The plasmid lacking the HindIII site is designated pUC19woH.

A 3207 bp BalI-AhaIII KEX2 fragment (obtainable from total genomic yeast DNA) is provided at both ends with BamHI linkers followed by a complete digestion with BamHI. Plasmid pUC19woH is cut to completion with BamHI, the linear 2690 bp fragment is isolated and ligated to the BamHI KEX2 fragment described above. An aliquot of the ligation mixture is transformed into *E. coli* JM101 cells. 12 transformed, ampicillin resistant colonies are grown in ampicillin (100 µg/ml) containing LB medium, plasmid DNA is extracted and analyzed by BamHI digests. One clone with the expected restriction fragments is selected and called pKS301b (deposited as DSM 6028).

The 2 µm yeast vector pAB24 which corresponds essentially to plasmid pDP34 (deposited as DSM 4473) is cut to completion with BamHI and the linear pAB24 fragment is isolated. Plasmid pKS301b is digested with BamHI and the fragment containing the complete KEX2 gene is isolated and ligated to the linearized yeast vector pAB24.An aliquot of the ligation mixture is transformed into *E. coli* JM101 and plasmid DNA of twelve positive clones is examined by BamHI digests. One clone with the expected restriction fragments is referred to as pAB226.

Plasmid pKS301b is digested to completion with SphI, PvuII and SeaI. The 2.37 kb SphI-PvuII fragment containing KEX2 sequences from −502 to +1843 and a part of the pUC19 polylinker is isolated. Plasmid pUC18 [Boehringer Mannheim, FRG] is cut to completion with SphI and SmaI. The 2660 bp SphI-SmaI pUC18 fragment is ligated to the 2.37 kb SphI-PvuII KEX2 fragment by SphI/SphI and PvuII/SmaI ligation. The PvuII/SmaI ligation results in the fusion of the KEX2 ORF coding for 614 amino acids to an ORF in the pUC18 sequences which codes for 7 additional C-terminal amino acids (-G-V-P-S-S-N-S) and is followed by a stop codon (TAA). An aliquot of the ligation mixture is transformed into *E. coli* JM101. Plasmid DNA is isolated from ampicillin resistant *E. coli* transformants and analyzed by digestion with SphI and EcoRI as well as with HindIII. One clone with the expected restriction pattern is referred to as p18kexp. In the sequence listing under SEQ ID No. 1 the ORF encoding the soluble KEX2$p_s$ with KEX2-derived DNA is shown.

Plasmid p18kexp is cut to completion with PvuII, SalI and ScaI. The 2552 bp SalI-PvuII fragment containing the KEX2 sequences reaching from −502 to +1843 as well as 206 bp of pUC18 sequences is isolated. Plasmid pDP34 is digested with BamHI and the ends of the linearized plasmid are filled in. After inactivation of T4 polymerase the linearized filled-in plasmid is cut with SalI and the 11.78 kb fragment is isolated. The pDP34 BamHI*-SalI fragment (BamHI*: filled-in BamHI) is ligated to the 2552 bp SalI-PvuII fragment by SalI/SalI and BamHI*PvuII ligation. An aliquot of the ligation mixture is transformed into transformation competent E. coli JM101 cells. Plasmid DNA is extracted from ampicillin resistant cells and analyzed by restriction analysis with SalI, NcoI, SmaI, XbaI, EcoRL. One clone with the expected restriction fragments is referred to as pDPkexp.

EXAMPLE 2

Construction of pDPkexpHDEL

Plasmid p18kexp (see example 1) consists of the truncated KEX2 gene coding for soluble KEX2p (KEX2p$_s$) inserted into the polylinker region of pUC18. The DNA sequence coding for the C-terminal end of KEX2p$_s$ in p 18kexp is followed by an Asp718 and an EcoRI site (see SEQ ID No. 1). The plasmid is cut with Asp718 and EcoRI and is ligated with the hybridized oligonucleotides with SEQ ID No. 11 and 12, encoding the HDEL sequence and two stop codons, resulting in the ligation product p 18kexpHDEL. Plasmids p18kexp and p18kexpHDEL can be distinguished by SacI or SfuI digestion. The polylinker insertion region was sequenced in p18kexpHDEL.

Plasmid p18kexpHDEL was cut with SalI, PvuII and ScaI and the 2572 bp SalI-PvuII fragment was isolated.

Plasmid pDP34 was cut with BamHI and the sticky ends were filled in with Klenow polymerase. After filling in, the polymerase was destroyed by phenol/chlorophorm and chlorophorm extractions followed by an ethanol precipitation. The BamHI cut filled in pDP34 fragment was then digested with SalI and the 11780 bp SalI-BamHI* (BamHI*: filled in BamHI site) was isolated.

The 2572 SalI-PvuII fragment isolated from p18kexpHDEL was ligated with the 11780 bp SalI-BamHI* pDP34 fragment. Ligation of SalI/SalI and PvuII/BamHI* led to the plasmid pDPkexpHDEL.

EXAMPLE 3

Construction of an yeast vector containing the IGF-1 expression cassette

Plasmid pDP34 is an E. coli—S. cerevisiae shuttle vector containing the complete 2 μ sequence, the yeast genomic URA3 and d LEU2 sequences as selectable markers for yeast, and pBR322 sequences for selection and propagation in E. coli [A. Hinnen, B. Meyhack and J. Heim, in Yeast genetic engineering (P. J. Barr, A. J. Brake & P. Valenzuela, eds., pp. 193–213 (1989), Butterworth Publishers, Stoneham]. A 276 bp SalI-BamHI fragment of pBR322 [Boehringer Mannheim GmbH, Germany] is ligated to the isolated linear vector afar digestion with SalI and BamHI. An aliquot of the ligation mixture is added to calcium-treated transformation competent E. coli HB101 cells [Invitrogen, San Diego, USA]. Four transformed ampicillin resistant E. coli transformants are grown in the presence of 100 μg/ml ampicillin. Plasmid DNA is prepared and analysed by digestion with SalI-BamHI. One plasmid having the expected restriction fragments is referred to as pDP34A. The human insulin-like growth factor-1 (IGF-1) gene expression cassette, for expression in yeast, is ligated into the BamHI site of pDP34A. The DNA sequence of the expression cassette,

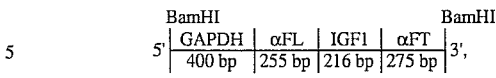

is shown under SEQ ID No. 5. It consists of a BamHI-cleavable linker, followed by an about 400 bp fragment of the S. cerevisiae glyceraldehyde-3-phosphate dehydrogenase (GAPDH) promoter, then the S. cerevisiae α-factor leader sequence encoding the first 85 amino acids of the α-factor precursor (J. Kurjan et al., Cell 30:933–943, 1982), directly followed by a chemically synthesized IGF-1 gene [G. T. Mullenbach, A. L. Choo, M. S. Urdea, P. J. Barr, J. P. Merryweather, A. J. Brake, and P. Valenzuela, Fed. Proc. 42, 434 (abstr.) (1983)], the about 275 bp S. cerevisiae α-factor terminator (αFT; Kurian et al., Cell 30:933–943, 1982) and a second BamHI-cleavable linker. An aliquot of the ligation mixture is transformed in E. coli HB101. Plasmid DNA from 6 independent transformants is analysed with SalI as well as BamHI. One clone with the promoter of the expression cassette oriented 3' to the SalI-BamHI fragment is named pDP34A/GAPDH-αFL-IGF1 -αFT.

EXAMPLE 4

Construction of two mutated α-factor leader sequences

A 1146 bp BamHI fragment, consisting of the 400 bp GAPDH promoter, the 255 bp αFL sequence, the 216 bp chemically synthesized IGF-1 gene (IGF-1 gene and 2 stop codons) and the 275 bp αFT, released from pDP34A/GAPDH-αFL-IGF1-αFT (see example 3). It is ligated to BamHI digested, bacterial alkaline phosphatase (Gibco-BRL, Basel, Switzerland) treated replicative form (RF) of phage vector M13mp18 (Boehringer Mannheim GmbH, Germany). An aliquot of the ligation mixture is transformed in E. coli JM101. Plasmid DNA from 6 plaques is analysed with ECORI, BamHI, and BamHI-SalI. One RF clone with the appropriate restriction fragments and with the promoter directly adjacent to the EcoRI site of the vector is selected and called mp18/BamHI/GAPDH-αFL-IGF1-αFT. Site-directed mutagenesis using the two-primer protocol [M. J. Zoller and M. Smith, Meth. in Enzymol. 154, 329–350 (1987)] employing the mutagenic oligodesoxyribonucleotide primer with SEQ ID No. 6 gives a new sequence of the αFL, changing the amino acids Ala[20] to Asp[20] and Pro[21] to Leu[21]. Single-stranded DNA obtained from one positive clone after hybridization with the radioactively labelled mutagenic primer is sequenced [F. Sanger, S. Nicklen and A. R. Coulsen, Proc, Natl. Acad. Sci. U.S.A. 74, 5463–5467 (1977)] to confirm the desired mutations. The mutated αFL sequence is named αFLMut2 and the resultant phage is called mp18/BamHI/GAPDH-αFLMut2-IGF1-αFT.

Site-directed mutagenesis using the four mutagenic oligodesoxyribonucleotide primers with SEQ ID No. 7, 8, 9 and 10 yields an αFL sequence in which the following amino acids are exchanged:
Ala[13] to Asn[13], Gln[32] to Ash[32], Pro[34] to Thr[34], Gly[40] to Asn[40], Lys[76] to Asn[76], and Glu[78] to Thr[78].

DNA sequencing on single-stranded DNA template confirms all mutations.

The mutated αFL sequence is named αFLG1G2G3G5 and the phage is referred to as mp18/BamHI/GAPDH-αFLG 1G2G3G5-IGF1-αFT.

EXAMPLE 5

Construction of yeast vectors containing GAPDH-αFL-IGF1-αFT, GAPDH-αFLMut2-IGF1-αFT, and GAPDH-αFLG1G2G3G5-IGF1-αFT To create an unique BglII site in the vector pDP34A (see example 3), plasmid DNA is digested to completion with SacI and the 3' overhang is flushed with T4 DNA polymerase (New England BioLabs, Beverly, Mass., USA). The linearized blunt-ended vector pDP34A is ligated to BglII linkers (Boehringer Mannheim GmbH, Germany). After linker ligation, the vector DNA is digested with BglII and then religated. Plasmid DNA of 6 ampicillin resistant transformants, obtained after transformation of an aliquot of the religated mixture in E. coli HB101, is analysed with restriction enzymes BglII-SalI and BglII-ScaI. One clone with the expected restriction fragments, confirming the creation of a BglII site in place of the SacI site, is designated as pDP34B.

pDP34B is digested to completion with BamHI and is treated with bacterial alkaline phosphatase. This linearized vector DNA is used to subclone the 1146 bp BamHI fragments obtained from pDP34A/GAPDH-αFL-IGF1-αFT (see example 3), mp18/BamHI/GAPDH-αFLMut2-IGF1-αFT (see example 4) and mp18/BamHI/GAPDH-αFLG1G2G3G5-IGF1-αFT (see example 4). After ligation, an aliquot from each of the three ligation mixtures is transformed in E. coli HB101. Plasmid DNA of four individual transformants from each of the three ligations are analysed by SalI to determine the orientation of the BamH fragments with respect to the SalI-BamHI pBR322 fragment. Plasmids yielding a 1147 bp fragment, with the pBR322 DNA at the 5' end of the promoter, are chosen and are named pDP34B/BamHI/GAPDH-αFL-IGF1-αFT, pDP34B/BamHI/GAPDH-αFLMut2-IGF1-αFT, and pDP34B/BamHI/GAPDH-αFLG1G2G3G5- IGF1-αFT.

EXAMPLE 6

Construction of yeast vectors which contain, on the same plasmid, expression cassettes for KEX2p and for IGF-1 with the wild type α-factor leader secretion signal The yeast vector pDP34B (example 5) is digested to completion with BglII and treated with bacterial alkaline phosphatase. Plasmid pKS301b (example 1) is digested with BamHI and the ~3210 bp fragment containing the complete KEX2 gene is isolated and ligated to the linearized vector pDP34B. An aliquot of the ligation mixture is transformed into E. coli HB101 and plasmid DNA of four transformants is examined by restriction analysis with BamHI and BglII. One clone with the expected restriction fragments is known as pDP34B/KEX2.

pDP34B/KEX2 is digested to completion with BamHI and treated with bacterial alkaline phosphatase.

A 1146 bp BamHI fragment containing the IGF-1 expression cassette isolated from pDP34A/GAPDH-αFL-IGF1-αFT (example 3) is ligated to linearized vector pDP34B/KEX2. After transformation, plasmid DNA of four clones is analysed with SalI and BamHI-BglII. One clone, with the promoter in the IGF-1 expression cassette 3' to the pBR322 SalI-BamHI fragment and the KEX2 gene in the opposite orientation to the IGF-1 cassette, is chosen and is named, pDP34B/KEX2/GAPDH-αFL-IGF1-αFT.

EXAMPLE 7

Construction of yeast vectors which contain, on the same plasmid, expression cassettes for KEX2p, and for IGF-1 with the wild type α-factor leader secretion signal After digestion of plasmid pDPkexp (example 1) with SmaI, BamHI linkers [Boehringer Mannheim GmbH, Germany] are added, followed by digestion with BamHI and ScaI which allows isolation of a ~2560 bp BamHI fragment. This is ligated to linearized pDP34B. Analysis of plasmid DNA of transformants with BamHI and BamHI-BglII yields one clone with the expected restriction fragments which is named pDP34B/kexp.

The IGF-1 expression cassette is subcloned in the BamHI site of pDP34B/kexp in the same way as in example 6. Restriction analysis with SalI and BamHI-BglII yields different clones with the promoter of the IGF-1 expression cassette 3' to the pBR322 SalI-BamHI fragment and the soluble KEX2 in the opposite orientation to the IGF-1 cassette. One such clone is chosen and is named pDP34B/kexp/GAPDH-αFL-IGF1-αFT.

EXAMPLE 8

Construction of yeast vectors which contain, on the same plasmid, expression cassettes for KEX2p$_s$HDEL and for IGF-1 with the wild type α-factor leader secretion signal pDPkexpHDEL (see example 2) is digested with BamHI, and after isolation of the about 2580 bp long fragment it is ligated to linearized pDP34B. Plasmid DNA of E. coli HB101 transformants are analysed with BamHI-BglII. One clone with the expected restriction fragments is named pDP34B/kexpHDEL.

The IGF-1 expression cassette is subcloned in the BamHI site of pDP34B/kexpHDEL in the same way as in example 6. Plasmid DNA of ampicillin resistant E. coli HB101 transformants is analysed with SalI and BamHI-BglII. One clone with the promoter of the IGF-1 expression cassette 3' to the pBR322 SalI-BamHI fragment and the soluble KEX2HDEL in the opposite orientation to the IGF-1 cassette is referred to as pDP34B/kex2pHDEL/GAPDH-αFL-IGF1-αFT.

EXAMPLE 9

Construction of plasmids pDP34B/KEX2/GAPDH-αFL-Mut2-IGF1-αFT, pDP34B/kexp/GAPDH-αFLMut2-IGF1-αFT, pDP34B/kexpHDEL/GAPDH-αFLMut2-IGF1-αFT, pDP34B/KEX2/GAPDH-αFLG1G2G3G5-IGF1-αFT, pDP34B/kexp/GAPDH-αFLG1G2G3G5-IGF1-αFT, and pDP34BP/kexpHDEL/GAPDH-αFLG1G2G3G5-IGF1-αFT These plasmids are constructed in a way similar to the procedures detailed in examples 6, 7 and 8. The expression cassettes, BamHI fragments of GAPDH-αFLMut2-IGF1-αFT and GAPDH-αFLG1G2G3G5, are isolated from pDP34B/BamHI/GAPDH-αFLMut2-IGF1-αFT (see example 5) and pDP34B/BamHI/GAPDH-αFLG1G2G3G5-IGF1-αFT (see example 5) and subcloned in yeast vectors already containing KEX2, or soluble KEX2 or soluble KEX2HDEL genes.

EXAMPLE 10

Construction of a kex2⁻ mutant of the yeast strain AB110 pKS301b (example 1) is cut at the unique BglII site in the KEX2 gene. A ~2920 bp BglII fragment from the plasmid YEp13 [J. Broach et at., Gene 8, 121–133 (1979)] is ligated to the linearized vector pKS301b. An aliquot of the ligation mixture is transformed in E. coli HB101. Plasmid DNA from twelve ampicillin resistant transformants are analysed with HindIII-EcoRI. One clone with the expected fragments is referred to as pUC19/kex2::LEU2. This plasmid has the coding sequence of the KEX2 gene disrupted by the functional LEU2 gene.

pUC19/kex2::LEU2 is digested with BamHI to release the linear kex2::LEU2 fragment. The yeast strain AB110 is used for transformation (example 11) with the linearized DNA. Transformants are selected for leucine prototrophy. Genomic DNA of four LEU2+ transformants are digested by EcoRI-HindIII. To confirm that the genomic copy of KEX2 is indeed disrupted by the LEU2 gene, Southern blot analysis is performed. One yeast transformants with the expected restriction fragments is named AB110 kex2−.

EXAMPLE 11

Transformation of *S. cerevisiae* strains AB110 and AB110 kex2−

Yeast transformation is carried out as described by Klebe et al. [Gene 25, 333–341 (1983)].

*S. cerevisiae* AB110 is transformed (see example 12) with the plasmids compiled hereinafter and the transformants are named as indicated:

| Plasmid | Transformant Name |
| --- | --- |
| pDP34B/GAPDH-αFL-IGF1-αFT (example 5) | yIG 1 |
| pDP34B/KEX2/GAPDH-αFL-IGF1-αFT (example 6) | yIG 2 |
| pDP34B/KEX2HDEL/GAPDH-αFL-IGF1-αFT (example 8) | yIG 3 |
| pDP34B/GAPDH-αFLMut2-IGF1-αFT (example 5) | yIG 4 |
| pDP34B/GAPDH-αFLG1G2G3G5-IGF1-αFT (example 5) | yIG 5 |

Three colonies of each of the transformants are selected and designated with an additional number (viz. yIG 1-1, yIG 1-2, yIG 1-3).

*S. cerevisiae* AB110 kex2− (see example 10) is transformed with the plasmids compiled hereinafter and the transformants are named as indicated:

| Plasmid | Transformant Name |
| --- | --- |
| pDP34B/GAPDH-αFL-IGF1-αFT (example 5) | yIG 6 |
| pDP34B/KEX2/GAPDH-αFL-IGF1-αFT (example 6) | yIG 7 |
| pDP34B/KEX2/GAPDH-αFLMut2-IGF1-αFT (example 9) | yIG 8 |
| pDP34B/kexp/GAPDH-αFLMut2-IGF1-αFT (example 9) | yIG 9 |
| pDP34B/kexpHDEL/GAPDH-αFLMut2-IGF1-αFT (ex. 9) | yIG 10 |
| pDP34B/KEX2/GAPDH-αFLG1G2G3G5-IGF1-αFT (ex. 9) | yIG 11 |
| pDP34B/kexp/GAPDH-αFLG1G2G3G5-IGF1-αFT (ex. 9) | YIG 12 |
| PDP34B/kexpHDEL/GAPDH-αFLG1G2G3G5-IGF1-αFT (ex. 9) | yIG 13 |

Three colonies of each of the transformants are selected and designated with an additional number (viz. yIG 6-1, yIG 6-2, yIG 6-3).

EXAMPLE 12

Growth of yeast transformants in shake-flask cultures and quantitative/qualitative determination of IGF-1 protein by high performance liquid chromatography (HPLC) Western blots

*S. cerevisiae* AB110 (Matα, his 4–580, leu2, ura 3–52, pep 4-3, [cir°]) is described elsewhere [P. J. Barr et at., J. Biol. Chem. 263, 16471–16478 (1988)]. A rich medium containing 6·5 g/l yeast extract, 4·5 g/l casamino acids and 30 g/l glucose is used as non-selective pre-culture medium. IGF-1 is expressed in the main culture which is a uracil-selective medium containing 1·7 g/l yeast nitrogen base supplemented with 30 g/l glucose, 8·5 g/l casamino acids and the required amino acids. Yeast transformants (see example 11) are grown at 30° C. on a rotary shaker at 180 rev./min. for 24 h in a 20 ml volume of the pre-culture medium and for 72 h in a 80 ml volume of main culture.

Aliquot of cells are harvested and the secreted, active monomeric IGF-1 molecule in the culture medium is measured by HPLC and ELISA [K. Steube et al., Eur. J. Biochem. 198, 651–657 (1991)].

Aliquots of grown cultures are centrifuged for 2 minutes at 13000×g. Cells are resuspended in 3×Laemmli buffer [6 % SDS, 0·15M Tris pH6·8, 6 mM EDTA, 30% glycerol, 0,05% bromophenol blue] and lysed by vigorous shaking with glass beads followed by incubation of the samples for 3 minutes in a boiling water bath. Protein from the cell lysate are separated by SDS-PAGE using a 15% polyacrylamide gel [U. K. Laemmli, Nature 227, 680–685 (1970)]. Proteins are electroblotted onto nitrocellulose filters with the aid of a semi-dry blotter [Sartorius GmbH, Germany]. The transferred proteins are detected with anti-IGF-1 antibodies following the procedure supplied by the Bio-Rad immune assay kit [Bio-Rad, Richmond, Calif., USA].

EXAMPLE 13

A comparison of secreted and intracellular IGF-1 protein(s) by HPLC and Western blot from transformants yIG 1, yIG 6, and yIG 7

Secreted IGF-1 from transformants of plasmid pDP34B/GAPDH-αFL-IGF1-αFT (see example 5) in yeast strains AB110 (transformants yIG 1-1, yIG 1-2 and yIG 1-3) and AB110 kex2− (transformants yIG 6-1, yIG 6-2 and yIG 6-3) are compared by HPLC and the results are depicted in Table 1.

TABLE 1

| Transformant | HPLC titer in mg/l |
| --- | --- |
| yIG 1-1 | 8 |
| yIG 1-2 | 7 |
| yIG 1-3 | 7 |
| yIG 6-1 | 0 |
| yIG 6-2 | 0 |
| yIG 6-3 | 0 |

Western blot analysis of intracellular protein from transformants yIG 6-1, yIG 6-2, and yIG 6-3 shows IGF-1 where the processing of the αFL has not occurred.

The results imply that no mature IGF-1 is secreted into the media from yeast strains which lack a functional copy of KEX2 on the chromosome. When a functional copy of KEX2 is reintroduced on a plasmid, eg. pDP34/KEX2/ GAPDH-αFL-IGF1-αFT (see example 6) into the yeast strain AB110 kex2⁻ (transformants yIG 7-1, yIG 7-2, and yIG 7-3) secreted IGF-1 is again observed.

EXAMPLE 14

A comparison of secreted IGF-1 protein by HPLC and ELISA from transformants yIG1, yIG2, and yIG3

HPLC measures the mount of active, monomeric IGF-1 in the supernatant. ELISA determines the total mount of IGF-1-like species in the supernatant. Besides the monomer, ELISA quantifies the mounts of intermolecular disulfide bridged dimers and multimers, malfolded IGF-1, oxidized IGF-1, and other molecules. Table 3 shows a comparison of the HPLC titres and ELISA values of see-feted IGF-1 from transformants co-expressing IGF-1 and KEX2 p (yIG 1 and yIG 2) and transformants co-expressing IGF-1 and soluble KEX2HDELp (yIG 3). The results are depicted in Table 2.

TABLE 2

| Transformants | HPLC titers in mg/l | ELISA values in mg/l |
| --- | --- | --- |
| yIG 1 | 9 | 98 |
| yIG 2 | 8 | 92 |
| yIG 3 | 9 | 27 |

These results are the avenge values obtained from 3 individual strains from each of the 3 transformations. Co-expression of soluble KEX2HDEL shows that formation of molecules other than monomers have been drastically reduced.

EXAMPLE 15

A comparison of secreted IGF-1 protein from transformants yIG 1, yIG 4, yIG 8, yIG 9 and yIG 10 by HPLC analysis The mutated leader sequence αFLMut2 does not allow secretion of IGF-1 in strain AB110. Glycosylated, unprocessed αFL-IGF-1 molecules accumulate inside the cell. From the nature of the glycosylation (only core-glycosylation observed), it is evident that these molecules have not traversed beyond the endoplasmatic reticulum due to mutations in the αFL sequence. Co-expression of IGF-1 using the αFLMut2 secretion signal, along with the three different forms of the KEX2 enzyme, KEX2, soluble KEX2 and soluble KEX2HDEL in AB110 kex2⁻, shows that the soluble KEX2HDEL protein is different from the other two.

Western blot analysis of intracellular IGF-1-like proteins from transformants yIG 1, yIG 4, yIG 8, yIG 9 and yIG 10 reveals that only soluble KEX2HDEL protein releases mature IGF-1 from the intracellular pool.

EXAMPLE 16

Analysis of secreted IGF-1 protein from transform ants yIG 1, yIG 5, yIG 11, yIG 12 and yIG 13 by HPLC analysis The mutated leader sequence αFLG1G2G3G5 allows poor secretion of IGF-1 in strain AB110. Unglycosylated, unprocessed αFL-IGF-1 molecules accumulate inside the cell. It appears that these molecules lack the signal sequence of the αFL, which signifies that translocation into the ER has occurred. However, entry into the ER has not caused glycosylation of the three possible sequons (Asn-X-Ser/Thr) in the proregion of the αFL. Co-expression of IGF-1 with three different forms of the KEX2. enzyme (KEX2, soluble KEX2 and soluble KEX2HDEL) in AB110 kex2⁻ shows that the soluble KEX2HDEL protein expressed in yIG 13 is unique in permitting more mature IGF-1 to be released from the intracellular pool.

EXAMPLE 17

A time course experiment to study the kinetics of secretion of monomeric IGF-1 from yeast transformants yIG 1, yIG 5 and yIG 13

The release of the proregion of the αFL from IGF-1 in the ER instead of in the Golgi may affect the total mount of monomeric IGF-1 secreted at different time points. It is probable that the proregion has a role in facilitating export of the unprocessed IGF-1 protein from the ER to the Golgi. To address this possibility, three individual strains from yIG 1, yIG 5 and yIG 13 are grown in shake flasks and the secretion of monomeric IGF-1 is measured by HPLC taking aliquots of supernatants from the yeast cultures after 40 h, 48 h, 60 h and 72h. The average values obtained from three individual strains (e.g. yIG 1-1, yIG 1-2, yIG 1-3, and yIG 5-1, yIG 5-2, yIG 5-3, and yIG 13-1, yIG 13-2, yIG 13-3), belonging to each of the three transformations, yIG 1, yIG 5 and yIG 13, are shown in Table 3.

TABLE 3

| Strain | Secreted IGF-1 (mg/l) after | | | |
| --- | --- | --- | --- | --- |
| | 40 h | 48 h | 60 h | 72 h |
| yIG 1 | 2.5 | 4 | 7 | 8.5 |
| yIG 5 | 0.8 | 1 | 1.2 | 1.5 |
| yIG 13 | 2.5 | 4.5 | 9.2 | 6 |

EXAMPLE 18

Analysis of secreted IGF-1 by Western blots shows appreciable decrease of dimeric forms using soluble KEX2HDEL protein Supernatants from yIG 1 and yIG 13 (example 17) have been analysed by Western blots under non-reducing and reducing conditions.

At time points 40 h, 48 h, and 60 h the formation of intermolecular disulphide bridged IGF-1 molecules is not observed using soluble KEX2HDEL protein. Only at 72 h does one see a negligible amount (barely visible on the blot) of dimeric IGF-1. However, strains expressing KEX2p do show dimers at every time point. These dimers can be reduced by dithiothreitol (DTT) implying that the dimers are indeed disulfide bonded.

Deposited Microorganisms

The following microorganism strains am deposited according to the Budapest Treaty at the Deutsche Sammlung von Milcroorganismen (DSM), Mascheroder Weg 1b, D-3300 Braunschweig (deposition dates and accession numbers given):

*Escherichia coli* JM109/pDP34: Mar. 14, 1988, DSM 4473.

*Escherichia coli* JM101/pKS301b: Jun. 25, 1990, DSM 6028.

5,618,690

What is claimed is:

1. A process for the preparation of a heterologous protein cleaved off a pro-sequence in a host cell, said process comprising the use of a host cell having an ER-located dibasic processing endoprotease for said cleavage, said ER-located endoprotease consisting of a dibasic processing endoprotease fused to an ER retention signal.

2. A process according to claim 1 comprising the use of a yeast host cell having an ER-located KEX2 or YAP3 protease.

3. A process according to claim 1 comprising the use of a yeast host cell having an ER-located KEX2 protease.

4. A process according to claim 1 for the preparation of heterologous biologically active protein cleaved off a yeast α-factor pro-sequence.

5. A process according to claim 1 for the preparation of an insulin-related protein.

* * * * *

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 1866 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..1866
        ( D ) OTHER INFORMATION: /product= "soluble KEX2"

( x i ) SEQUENCE DESCRIPTION: SEQ ID NO:1:

```
ATG AAA GTG AGG AAA TAT ATT ACT TTA TGC TTT TGG TGG GCC TTT TCA    48
Met Lys Val Arg Lys Tyr Ile Thr Leu Cys Phe Trp Trp Ala Phe Ser
 1               5                  10                  15

ACA TCC GCT CTT GTA TCA TCA CAA CAA ATT CCA TTG AAG GAC CAT ACG    96
Thr Ser Ala Leu Val Ser Ser Gln Gln Ile Pro Leu Lys Asp His Thr
             20                  25                  30

TCA CGA CAG TAT TTT GCT GTA GAA AGC AAT GAA ACA TTA TCC CGC TTG   144
Ser Arg Gln Tyr Phe Ala Val Glu Ser Asn Glu Thr Leu Ser Arg Leu
         35                  40                  45

GAG GAA ATG CAT CCA AAT TGG AAA TAT GAA CAT GAT GTT CGA GGG CTA   192
Glu Glu Met His Pro Asn Trp Lys Tyr Glu His Asp Val Arg Gly Leu
     50                  55                  60

CCA AAC CAT TAT GTT TTT TCA AAA GAG TTG CTA AAA TTG GGC AAA AGA   240
Pro Asn His Tyr Val Phe Ser Lys Glu Leu Leu Lys Leu Gly Lys Arg
 65                  70                  75                  80

TCA TCA TTA GAA GAG TTA CAG GGG GAT AAC AAC GAC CAC ATA TTA TCT   288
Ser Ser Leu Glu Glu Leu Gln Gly Asp Asn Asn Asp His Ile Leu Ser
                 85                  90                  95

GTC CAT GAT TTA TTC CCG CGT AAC GAC CTA TTT AAG AGA CTA CCG GTG   336
Val His Asp Leu Phe Pro Arg Asn Asp Leu Phe Lys Arg Leu Pro Val
            100                 105                 110

CCT GCT CCA CCA ATG GAC TCA AGC TTG TTA CCG GTA AAA GAA GCT GAG   384
Pro Ala Pro Pro Met Asp Ser Ser Leu Leu Pro Val Lys Glu Ala Glu
        115                 120                 125

GAT AAA CTC AGC ATA AAT GAT CCG CTT TTT GAG AGG CAG TGG CAC TTG   432
Asp Lys Leu Ser Ile Asn Asp Pro Leu Phe Glu Arg Gln Trp His Leu
    130                 135                 140

GTC AAT CCA AGT TTT CCT GGC AGT GAT ATA AAT GTT CTT GAT CTG TGG   480
Val Asn Pro Ser Phe Pro Gly Ser Asp Ile Asn Val Leu Asp Leu Trp
145                 150                 155                 160

TAC AAT AAT ATT ACA GGC GCA GGG GTC GTG GCT GCC ATT GTT GAT GAT   528
Tyr Asn Asn Ile Thr Gly Ala Gly Val Val Ala Ala Ile Val Asp Asp
                165                 170                 175

GGC CTT GAC TAC GAA AAT GAA GAC TTG AAG GAT AAT TTT TGC GCT GAA   576
Gly Leu Asp Tyr Glu Asn Glu Asp Leu Lys Asp Asn Phe Cys Ala Glu
            180                 185                 190

GGT TCT TGG GAT TTC AAC GAC AAT ACC AAT TTA CCT AAA CCA AGA TTA   624
Gly Ser Trp Asp Phe Asn Asp Asn Thr Asn Leu Pro Lys Pro Arg Leu
        195                 200                 205

TCT GAT GAC TAC CAT GGT ACG AGA TGT GCA GGT GAA ATA GCT GCC AAA   672
Ser Asp Asp Tyr His Gly Thr Arg Cys Ala Gly Glu Ile Ala Ala Lys
    210                 215                 220
```

| | | | | | | | | | | | | | | | | |
|---|---|---|---|---|---|---|---|---|---|---|---|---|---|---|---|---|
| AAA | GGT | AAC | AAT | TTT | TGC | GGT | GTC | GGG | GTA | GGT | TAC | AAC | GCT | AAA | ATC | 720 |
| Lys 225 | Gly | Asn | Asn | Phe | Cys 230 | Gly | Val | Gly | Val 235 | Gly | Tyr | Asn | Ala | Lys | Ile 240 | |
| TCA | GGC | ATA | AGA | ATC | TTA | TCC | GGT | GAT | ATC | ACT | ACG | GAA | GAT | GAA | GCT | 768 |
| Ser | Gly | Ile | Arg 245 | Ile | Leu | Ser | Gly | Asp | Ile 250 | Thr | Thr | Glu | Asp | Glu 255 | Ala | |
| GCG | TCC | TTG | ATT | TAT | GGT | CTA | GAC | GTA | AAC | GAT | ATA | TAT | TCA | TGC | TCA | 816 |
| Ala | Ser | Leu | Ile 260 | Tyr | Gly | Leu | Asp | Val 265 | Asn | Asp | Ile | Tyr | Ser 270 | Cys | Ser | |
| TGG | GGT | CCC | GCT | GAT | GAC | GGA | AGA | CAT | TTA | CAA | GGC | CCT | AGT | GAC | CTG | 864 |
| Trp | Gly | Pro 275 | Ala | Asp | Asp | Gly | Arg 280 | His | Leu | Gln | Gly | Pro 285 | Ser | Asp | Leu | |
| GTG | AAA | AAG | GCT | TTA | GTA | AAA | GGT | GTT | ACT | GAG | GGA | AGA | GAT | TCC | AAA | 912 |
| Val | Lys 290 | Lys | Ala | Leu | Val 295 | Lys | Gly | Val | Thr | Glu 300 | Gly | Arg | Asp | Ser | Lys | |
| GGA | GCG | ATT | TAC | GTT | TTT | GCC | AGT | GGA | AAT | GGT | GGA | ACT | CGT | GGT | GAT | 960 |
| Gly 305 | Ala | Ile | Tyr | Val 310 | Phe | Ala | Ser | Gly | Asn 315 | Gly | Gly | Thr | Arg | Gly 320 | Asp | |
| AAT | TGC | AAT | TAC | GAC | GGC | TAT | ACT | AAT | TCC | ATA | TAT | TCT | ATT | ACT | ATT | 1008 |
| Asn | Cys | Asn | Tyr | Asp 325 | Gly | Tyr | Thr | Asn | Ser 330 | Ile | Tyr | Ser | Ile | Thr 335 | Ile | |
| GGG | GCT | ATT | GAT | CAC | AAA | GAT | CTA | CAT | CCT | CCT | TAT | TCC | GAA | GGT | TGT | 1056 |
| Gly | Ala | Ile | Asp 340 | His | Lys | Asp | Leu | His 345 | Pro | Pro | Tyr | Ser | Glu 350 | Gly | Cys | |
| TCC | GCC | GTC | ATG | GCA | GTC | ACG | TAT | TCT | TCA | GGT | TCA | GGC | GAA | TAT | ATT | 1104 |
| Ser | Ala | Val 355 | Met | Ala | Val | Thr | Tyr 360 | Ser | Ser | Gly | Ser | Gly 365 | Glu | Tyr | Ile | |
| CAT | TCG | AGT | GAT | ATC | AAC | GGC | AGA | TGC | AGT | AAT | AGC | CAC | GGT | GGA | ACG | 1152 |
| His | Ser | Ser 370 | Asp | Ile | Asn | Gly | Arg 375 | Cys | Ser | Asn | Ser | His 380 | Gly | Gly | Thr | |
| TCT | GCG | GCT | GCT | CCA | TTA | GCT | GCC | GGT | GTT | TAC | ACT | TTG | TTA | CTA | GAA | 1200 |
| Ser 385 | Ala | Ala | Ala | Pro | Leu 390 | Ala | Ala | Gly | Val | Tyr 395 | Thr | Leu | Leu | Leu | Glu 400 | |
| GCC | AAC | CCA | AAC | CTA | ACT | TGG | AGA | GAC | GTA | CAG | TAT | TTA | TCA | ATC | TTG | 1248 |
| Ala | Asn | Pro | Asn | Leu 405 | Thr | Trp | Arg | Asp | Val 410 | Gln | Tyr | Leu | Ser | Ile 415 | Leu | |
| TCT | GCG | GTA | GGG | TTA | GAA | AAG | AAC | GCT | GAC | GGA | GAT | TGG | AGA | GAT | AGC | 1296 |
| Ser | Ala | Val | Gly 420 | Leu | Glu | Lys | Asn | Ala 425 | Asp | Gly | Asp | Trp | Arg 430 | Asp | Ser | |
| GCC | ATG | GGG | AAG | AAA | TAC | TCT | CAT | CGC | TAT | GGC | TTT | GGT | AAA | ATC | GAT | 1344 |
| Ala | Met | Gly 435 | Lys | Lys | Tyr | Ser | His 440 | Arg | Tyr | Gly | Phe | Gly 445 | Lys | Ile | Asp | |
| GCC | CAT | AAG | TTA | ATT | GAA | ATG | TCC | AAG | ACC | TGG | GAG | AAT | GTT | AAC | GCA | 1392 |
| Ala | His 450 | Lys | Leu | Ile | Glu | Met 455 | Ser | Lys | Thr | Trp | Glu 460 | Asn | Val | Asn | Ala | |
| CAA | ACC | TGG | TTT | TAC | CTG | CCA | ACA | TTG | TAT | GTT | TCC | CAG | TCC | ACA | AAC | 1440 |
| Gln | Thr | Trp | Phe | Tyr 470 | Leu | Pro | Thr | Leu | Tyr 475 | Val | Ser | Gln | Ser | Thr | Asn 480 | |
| Gln 465 | | | | | | | | | | | | | | | | |
| TCC | ACG | GAA | GAG | ACA | TTA | GAA | TCC | GTC | ATA | ACC | ATA | TCA | GAA | AAA | AGT | 1488 |
| Ser | Thr | Glu | Glu | Thr 485 | Leu | Glu | Ser | Val | Ile 490 | Thr | Ile | Ser | Glu | Lys 495 | Ser | |
| CTT | CAA | GAT | GCT | AAC | TTC | AAG | AGA | ATT | GAG | CAC | GTC | ACG | GTA | ACT | GTA | 1536 |
| Leu | Gln | Asp | Ala 500 | Asn | Phe | Lys | Arg | Ile 505 | Glu | His | Val | Thr | Val 510 | Thr | Val | |
| GAT | ATT | GAT | ACA | GAA | ATT | AGG | GGA | ACT | ACG | ACT | GTC | GAT | TTA | ATA | TCA | 1584 |
| Asp | Ile | Asp | Thr 515 | Glu | Ile | Arg | Gly | Thr 520 | Thr | Thr | Val | Asp | Leu 525 | Ile | Ser | |
| CCA | GCG | GGG | ATA | ATT | TCA | AAC | CTT | GGC | GTT | GTA | AGA | CCA | AGA | GAT | GTT | 1632 |
| Pro | Ala | Gly | Ile 530 | Ile | Ser | Asn | Leu | Gly 535 | Val | Val | Arg | Pro | Arg 540 | Asp | Val | |

| | | | | | | | | | | | | | | | | |
|---|---|---|---|---|---|---|---|---|---|---|---|---|---|---|---|---|
| TCA | TCA | GAG | GGA | TTC | AAA | GAC | TGG | ACA | TTC | ATG | TCT | GTA | GCA | CAT | TGG | 1680 |
| Ser | Ser | Glu | Gly | Phe | Lys | Asp | Trp | Thr | Phe | Met | Ser | Val | Ala | His | Trp | |
| 545 | | | | 550 | | | | | 555 | | | | | 560 | | |
| GGT | GAG | AAC | GGC | GTA | GGT | GAT | TGG | AAA | ATC | AAG | GTT | AAG | ACA | ACA | GAA | 1728 |
| Gly | Glu | Asn | Gly | Val | Gly | Asp | Trp | Lys | Ile | Lys | Val | Lys | Thr | Thr | Glu | |
| | | | | 565 | | | | 570 | | | | | 575 | | | |
| AAT | GGA | CAC | AGG | ATT | GAC | TTC | CAC | AGT | TGG | AGG | CTG | AAG | CTC | TTT | GGG | 1776 |
| Asn | Gly | His | Arg | Ile | Asp | Phe | His | Ser | Trp | Arg | Leu | Lys | Leu | Phe | Gly | |
| | | | 580 | | | | | 585 | | | | | 590 | | | |
| GAA | TCC | ATT | GAT | TCA | TCT | AAA | ACA | GAA | ACT | TTC | GTC | TTT | GGA | AAC | GAT | 1824 |
| Glu | Ser | Ile | Asp | Ser | Ser | Lys | Thr | Glu | Thr | Phe | Val | Phe | Gly | Asn | Asp | |
| | | 595 | | | | | 600 | | | | | 605 | | | | |
| AAA | GAG | GAG | GTT | GAA | CCA | GGG | GTA | CCG | AGC | TCG | AAT | TCG | TAA | | | 1866 |
| Lys | Glu | Glu | Val | Glu | Pro | Gly | Val | Pro | Ser | Ser | Asn | Ser | | | | |
| 610 | | | | | 615 | | | | | 620 | | | | | | |

(2) INFORMATION FOR SEQ ID NO:2:

(i) SEQUENCE CHARACTERISTICS:
        (A) LENGTH: 621 amino acids
        (B) TYPE: amino acid
        (D) TOPOLOGY: linear (ii) MOLECULE TYPE: protein (xi) SEQUENCE DESCRIPTION: SEQ ID NO:2:

| | | | | | | | | | | | | | | | |
|---|---|---|---|---|---|---|---|---|---|---|---|---|---|---|---|
| Met | Lys | Val | Arg | Lys | Tyr | Ile | Thr | Leu | Cys | Phe | Trp | Trp | Ala | Phe | Ser |
| 1 | | | | 5 | | | | | 10 | | | | | 15 | |
| Thr | Ser | Ala | Leu | Val | Ser | Ser | Gln | Gln | Ile | Pro | Leu | Lys | Asp | His | Thr |
| | | | | 20 | | | | | 25 | | | | | 30 | |
| Ser | Arg | Gln | Tyr | Phe | Ala | Val | Glu | Ser | Asn | Glu | Thr | Leu | Ser | Arg | Leu |
| | | | 35 | | | | | 40 | | | | | 45 | | |
| Glu | Glu | Met | His | Pro | Asn | Trp | Lys | Tyr | Glu | His | Asp | Val | Arg | Gly | Leu |
| | 50 | | | | | 55 | | | | | 60 | | | | |
| Pro | Asn | His | Tyr | Val | Phe | Ser | Lys | Glu | Leu | Leu | Lys | Leu | Gly | Lys | Arg |
| 65 | | | | | 70 | | | | | 75 | | | | | 80 |
| Ser | Ser | Leu | Glu | Glu | Leu | Gln | Gly | Asp | Asn | Asn | Asp | His | Ile | Leu | Ser |
| | | | | 85 | | | | | 90 | | | | | 95 | |
| Val | His | Asp | Leu | Phe | Pro | Arg | Asn | Asp | Leu | Phe | Lys | Arg | Leu | Pro | Val |
| | | | 100 | | | | | 105 | | | | | 110 | | |
| Pro | Ala | Pro | Pro | Met | Asp | Ser | Ser | Leu | Leu | Pro | Val | Lys | Glu | Ala | Glu |
| | | 115 | | | | | 120 | | | | | 125 | | | |
| Asp | Lys | Leu | Ser | Ile | Asn | Asp | Pro | Leu | Phe | Glu | Arg | Gln | Trp | His | Leu |
| | 130 | | | | | 135 | | | | | 140 | | | | |
| Val | Asn | Pro | Ser | Phe | Pro | Gly | Ser | Asp | Ile | Asn | Val | Leu | Asp | Leu | Trp |
| 145 | | | | | 150 | | | | | 155 | | | | | 160 |
| Tyr | Asn | Asn | Ile | Thr | Gly | Ala | Gly | Val | Val | Ala | Ala | Ile | Val | Asp | Asp |
| | | | | 165 | | | | | 170 | | | | | 175 | |
| Gly | Leu | Asp | Tyr | Glu | Asn | Glu | Asp | Leu | Lys | Asp | Asn | Phe | Cys | Ala | Glu |
| | | | 180 | | | | | 185 | | | | | 190 | | |
| Gly | Ser | Trp | Asp | Phe | Asn | Asp | Asn | Thr | Asn | Leu | Pro | Lys | Pro | Arg | Leu |
| | | 195 | | | | | 200 | | | | | 205 | | | |
| Ser | Asp | Asp | Tyr | His | Gly | Thr | Arg | Cys | Ala | Gly | Glu | Ile | Ala | Ala | Lys |
| | 210 | | | | | 215 | | | | | 220 | | | | |
| Lys | Gly | Asn | Asn | Phe | Cys | Gly | Val | Gly | Val | Gly | Tyr | Asn | Ala | Lys | Ile |
| 225 | | | | | 230 | | | | | 235 | | | | | 240 |
| Ser | Gly | Ile | Arg | Ile | Leu | Ser | Gly | Asp | Ile | Thr | Thr | Glu | Asp | Glu | Ala |
| | | | | 245 | | | | | 250 | | | | | 255 | |

```
Ala  Ser  Leu  Ile  Tyr  Gly  Leu  Asp  Val  Asn  Asp  Ile  Tyr  Ser  Cys  Ser
               260                      265                     270

Trp  Gly  Pro  Ala  Asp  Asp  Gly  Arg  His  Leu  Gln  Gly  Pro  Ser  Asp  Leu
          275                      280                     285

Val  Lys  Lys  Ala  Leu  Val  Lys  Gly  Val  Thr  Glu  Gly  Arg  Asp  Ser  Lys
     290                      295                     300

Gly  Ala  Ile  Tyr  Val  Phe  Ala  Ser  Gly  Asn  Gly  Gly  Thr  Arg  Gly  Asp
305                      310                     315                          320

Asn  Cys  Asn  Tyr  Asp  Gly  Tyr  Thr  Asn  Ser  Ile  Tyr  Ser  Ile  Thr  Ile
                    325                      330                     335

Gly  Ala  Ile  Asp  His  Lys  Asp  Leu  His  Pro  Pro  Tyr  Ser  Glu  Gly  Cys
               340                      345                     350

Ser  Ala  Val  Met  Ala  Val  Thr  Tyr  Ser  Ser  Gly  Ser  Gly  Glu  Tyr  Ile
          355                      360                     365

His  Ser  Ser  Asp  Ile  Asn  Gly  Arg  Cys  Ser  Asn  Ser  His  Gly  Gly  Thr
     370                      375                     380

Ser  Ala  Ala  Ala  Pro  Leu  Ala  Ala  Gly  Val  Tyr  Thr  Leu  Leu  Leu  Glu
385                      390                     395                          400

Ala  Asn  Pro  Asn  Leu  Thr  Trp  Arg  Asp  Val  Gln  Tyr  Leu  Ser  Ile  Leu
               405                      410                     415

Ser  Ala  Val  Gly  Leu  Glu  Lys  Asn  Ala  Asp  Gly  Asp  Trp  Arg  Asp  Ser
               420                      425                     430

Ala  Met  Gly  Lys  Lys  Tyr  Ser  His  Arg  Tyr  Gly  Phe  Gly  Lys  Ile  Asp
          435                      440                     445

Ala  His  Lys  Leu  Ile  Glu  Met  Ser  Lys  Thr  Trp  Glu  Asn  Val  Asn  Ala
     450                      455                     460

Gln  Thr  Trp  Phe  Tyr  Leu  Pro  Thr  Leu  Tyr  Val  Ser  Gln  Ser  Thr  Asn
465                      470                     475                          480

Ser  Thr  Glu  Glu  Thr  Leu  Glu  Ser  Val  Ile  Thr  Ile  Ser  Glu  Lys  Ser
               485                      490                     495

Leu  Gln  Asp  Ala  Asn  Phe  Lys  Arg  Ile  Glu  His  Val  Thr  Val  Thr  Val
               500                      505                     510

Asp  Ile  Asp  Thr  Glu  Ile  Arg  Gly  Thr  Thr  Thr  Val  Asp  Leu  Ile  Ser
          515                      520                     525

Pro  Ala  Gly  Ile  Ile  Ser  Asn  Leu  Gly  Val  Val  Arg  Pro  Arg  Asp  Val
     530                      535                     540

Ser  Ser  Glu  Gly  Phe  Lys  Asp  Trp  Thr  Phe  Met  Ser  Val  Ala  His  Trp
545                      550                     555                          560

Gly  Glu  Asn  Gly  Val  Gly  Asp  Trp  Lys  Ile  Lys  Val  Lys  Thr  Thr  Glu
                    565                      570                     575

Asn  Gly  His  Arg  Ile  Asp  Phe  His  Ser  Trp  Arg  Leu  Lys  Leu  Phe  Gly
               580                      585                     590

Glu  Ser  Ile  Asp  Ser  Ser  Lys  Thr  Glu  Thr  Phe  Val  Phe  Gly  Asn  Asp
          595                      600                     605

Lys  Glu  Glu  Val  Glu  Pro  Gly  Val  Pro  Ser  Ser  Asn  Ser
     610                      615                     620
```

( 2 ) INFORMATION FOR SEQ ID NO:3:

( i ) SEQUENCE CHARACTERISTICS:
        ( A ) LENGTH: 12 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
    ( A ) NAME/KEY: CDS
    ( B ) LOCATION: 1..12
    ( D ) OTHER INFORMATION: /function= "coding region for ER retention signal HDEL"

( x i ) SEQUENCE DESCRIPTION: SEQ ID NO:3:

```
CAC  GAC  GAA  TTA                                                          12
His  Asp  Glu  Leu
 1
```

( 2 ) INFORMATION FOR SEQ ID NO:4:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
His  Asp  Glu  Leu
 1
```

( 2 ) INFORMATION FOR SEQ ID NO:5:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: Kluyveromyces lactis ( i x ) FEATURE:
        ( A ) NAME/KEY: Domain
        ( B ) LOCATION: 1..4
        ( D ) OTHER INFORMATION: /note= "ER retention signal DDEL"

( x i ) SEQUENCE DESCRIPTION: SEQ ID NO:5:

```
Asp  Asp  Glu  Leu
 1
```

( 2 ) INFORMATION FOR SEQ ID NO:6:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( i x ) FEATURE:
        ( A ) NAME/KEY: Domain
        ( B ) LOCATION: 1..4
        ( D ) OTHER INFORMATION: /note= "ER retention signal KDEL"

( x i ) SEQUENCE DESCRIPTION: SEQ ID NO:6:

```
Lys  Asp  Glu  Leu
 1
```

( 2 ) INFORMATION FOR SEQ ID NO:7:

( i ) SEQUENCE CHARACTERISTICS:
        ( A ) LENGTH: 1158 base pairs
        ( B ) TYPE: nucleic acid
        ( C ) STRANDEDNESS: double
        ( D ) TOPOLOGY: linear -continued (i i) MOLECULE TYPE: DNA (genomic)

(i x) FEATURE:
    (A) NAME/KEY: CDS
    (B) LOCATION: 405..869

(x i) SEQUENCE DESCRIPTION: SEQ ID NO:7:

```
GGATCCCCAG CTTAGTTCAT AGGTCCATTC TCTTAGCGCA ACTACAGAGA ACAGGGGCAC      60

AAACAGGCAA AAAACGGGCA CAACCTCAAT GGAGTGATGC AACCTGCCTG GAGTAAATGA     120

TGACACAAGG CAATTGACCC ACGCATGTAT CTATCTCATT TTCTTACACC TTCTATTACC     180

TTCTGCTCTC TCTGATTTGG AAAAAGCTGA AAAAAAAGGT TGAAACCAGT TCCCTGAAAT     240

TATTCCCCTA CTTGACTAAT AAGTATATAA AGACGGTAGG TATTGATTGT AATTCTGTAA     300

ATCTATTTCT TAAACTTCTT AAATTCTACT TTTATAGTTA GTCTTTTTTT TAGTTTTAAA     360

ACACCAAGAA CTTAGTTTCG AATAAACACA CATAAACAAA CACC ATG AGA TTT CCT     416
                                                   Met Arg Phe Pro
                                                    1
```

```
TCA ATT TTT ACT GCA GTT TTA TTC GCA GCA TCC TCC GCA TTA GCT GCT     464
Ser Ile Phe Thr Ala Val Leu Phe Ala Ala Ser Ser Ala Leu Ala Ala
 5               10                  15                  20

CCA GTC AAC ACT ACA ACA GAA GAT GAA ACG GCA CAA ATT CCG GCT GAA     512
Pro Val Asn Thr Thr Thr Glu Asp Glu Thr Ala Gln Ile Pro Ala Glu
             25                  30                  35

GCT GTC ATC GGT TAC TTA GAT TTA GAA GGG GAT TTC GAT GTT GCT GTT     560
Ala Val Ile Gly Tyr Leu Asp Leu Glu Gly Asp Phe Asp Val Ala Val
         40                  45                  50

TTG CCA TTT TCC AAC AGC ACA AAT AAC GGG TTA TTG TTT ATA AAT ACT     608
Leu Pro Phe Ser Asn Ser Thr Asn Asn Gly Leu Leu Phe Ile Asn Thr
     55                  60                  65

ACT ATT GCC AGC ATT GCT GCT AAA GAA GAA GGG GTA CAG CTG GAT AAA     656
Thr Ile Ala Ser Ile Ala Ala Lys Glu Glu Gly Val Gln Leu Asp Lys
 70                  75                  80

AGA GGT CCA GAA ACC TTG TGT GGT GCT GAA TTG GTC GAT GCT TTG CAA     704
Arg Gly Pro Glu Thr Leu Cys Gly Ala Glu Leu Val Asp Ala Leu Gln
 85                  90                  95                 100

TTC GTT TGT GGT GAC AGA GGT TTC TAC TTC AAC AAG CCA ACC GGT TAC     752
Phe Val Cys Gly Asp Arg Gly Phe Tyr Phe Asn Lys Pro Thr Gly Tyr
            105                 110                 115

GGT TCT TCT TCT AGA AGA GCT CCA CAA ACC GGT ATC GTT GAC GAA TGT     800
Gly Ser Ser Ser Arg Arg Ala Pro Gln Thr Gly Ile Val Asp Glu Cys
        120                 125                 130

TGT TTC AGA TCT TGT GAC TTG AGA AGA TTG GAA ATG TAC TGT GCT CCA     848
Cys Phe Arg Ser Cys Asp Leu Arg Arg Leu Glu Met Tyr Cys Ala Pro
        135                 140                 145

TTG AAG CCA GCT AAG TCT GCT TGATAAGTCG ACTTTGTTCC CACTGTACTT     899
Leu Lys Pro Ala Lys Ser Ala
150                 155
```

```
TTAGCTCGTA CAAAATACAA TATACTTTTC ATTTCTCCGT AAACAACATG TTTTCCCATG     959

TAATATCCTT TTCTATTTTT CGTTCCGTTA CCAACTTTAC ACATACTTTA TATAGCTATT    1019

CACTTCTATA CACTAAAAAA CTAAGACAAT TTTAATTTTG CTGCCTGCCA TATTTCAATT    1079

TGTTATAAAT TCCTATAATT TATCCTATTA GTAGCTAAAA AAAGATGAAT GTGAATCGAA    1139

TCCTAAGAGA ATTGGATCC                                                  1158
```

(2) INFORMATION FOR SEQ ID NO:8:

(i) SEQUENCE CHARACTERISTICS:
        (A) LENGTH: 155 amino acids
        (B) TYPE: amino acid (D) TOPOLOGY: linear (ii) MOLECULE TYPE: protein (xi) SEQUENCE DESCRIPTION: SEQ ID NO:8:

| Met | Arg | Phe | Pro | Ser | Ile | Phe | Thr | Ala | Val | Leu | Phe | Ala | Ala | Ser | Ser |
|---|---|---|---|---|---|---|---|---|---|---|---|---|---|---|---|
| 1 | | | | 5 | | | | | 10 | | | | | 15 | |

| Ala | Leu | Ala | Ala | Pro | Val | Asn | Thr | Thr | Thr | Glu | Asp | Glu | Thr | Ala | Gln |
|---|---|---|---|---|---|---|---|---|---|---|---|---|---|---|---|
| | | | 20 | | | | | 25 | | | | | 30 | | |

| Ile | Pro | Ala | Glu | Ala | Val | Ile | Gly | Tyr | Leu | Asp | Leu | Glu | Gly | Asp | Phe |
|---|---|---|---|---|---|---|---|---|---|---|---|---|---|---|---|
| | | 35 | | | | | 40 | | | | | 45 | | | |

| Asp | Val | Ala | Val | Leu | Pro | Phe | Ser | Asn | Ser | Thr | Asn | Asn | Gly | Leu | Leu |
|---|---|---|---|---|---|---|---|---|---|---|---|---|---|---|---|
| | 50 | | | | | 55 | | | | | 60 | | | | |

| Phe | Ile | Asn | Thr | Thr | Ile | Ala | Ser | Ile | Ala | Ala | Lys | Glu | Glu | Gly | Val |
|---|---|---|---|---|---|---|---|---|---|---|---|---|---|---|---|
| 65 | | | | | 70 | | | | | 75 | | | | | 80 |

| Gln | Leu | Asp | Lys | Arg | Gly | Pro | Glu | Thr | Leu | Cys | Gly | Ala | Glu | Leu | Val |
|---|---|---|---|---|---|---|---|---|---|---|---|---|---|---|---|
| | | | | 85 | | | | | 90 | | | | | 95 | |

| Asp | Ala | Leu | Gln | Phe | Val | Cys | Gly | Asp | Arg | Gly | Phe | Tyr | Phe | Asn | Lys |
|---|---|---|---|---|---|---|---|---|---|---|---|---|---|---|---|
| | | | 100 | | | | | 105 | | | | | 110 | | |

| Pro | Thr | Gly | Tyr | Gly | Ser | Ser | Ser | Arg | Arg | Ala | Pro | Gln | Thr | Gly | Ile |
|---|---|---|---|---|---|---|---|---|---|---|---|---|---|---|---|
| | | 115 | | | | | 120 | | | | | 125 | | | |

| Val | Asp | Glu | Cys | Cys | Phe | Arg | Ser | Cys | Asp | Leu | Arg | Arg | Leu | Glu | Met |
|---|---|---|---|---|---|---|---|---|---|---|---|---|---|---|---|
| | 130 | | | | | 135 | | | | | 140 | | | | |

| Tyr | Cys | Ala | Pro | Leu | Lys | Pro | Ala | Lys | Ser | Ala |
|---|---|---|---|---|---|---|---|---|---|---|
| 145 | | | | | 150 | | | | | 155 |

(2) INFORMATION FOR SEQ ID NO:9:

(i) SEQUENCE CHARACTERISTICS:
(A) LENGTH: 31 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:9:

GTAGTGTTGA CTAGATCTGC TAATGCGGAG G                                31

(2) INFORMATION FOR SEQ ID NO:10:

(i) SEQUENCE CHARACTERISTICS:
(A) LENGTH: 26 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:10:

GCGGAGGATG CGTTGAATAA AACTGC                                     26

(2) INFORMATION FOR SEQ ID NO:11:

(i) SEQUENCE CHARACTERISTICS:
(A) LENGTH: 28 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:11:

CAGCTTCAGC AGTAATGTTT GCCGTTTC                                   28

( 2 ) INFORMATION FOR SEQ ID NO:12:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:12:

ATCTAAGTAG TTGATGACAG C                           21

( 2 ) INFORMATION FOR SEQ ID NO:13:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:13:

GCTGTACCCC GGTTTCGTTA GCAGCAATGC                  30

( 2 ) INFORMATION FOR SEQ ID NO:14:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:14:

GTACCGTTCG AACACGACGA ATTATAATAG                  30

( 2 ) INFORMATION FOR SEQ ID NO:15:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:15:

AATTCTATTA TAATTCGTCG TGTTCGAACG                  30